United States Patent
Keene et al.

(10) Patent No.: US 8,821,848 B1
(45) Date of Patent: Sep. 2, 2014

(54) FERRATE AND POVIDONE IODINE (PI) COMPOSITION

(71) Applicant: Biolife, L.L.C., Sarasota, FL (US)

(72) Inventors: Talmadge Kelly Keene, Apollo Beach, FL (US); John Hen, Bradenton, FL (US)

(73) Assignee: Biolife, L.L.C., Sarasota, FL (US)

( * ) Notice: Subject to any disclaimer, the term of this patent is extended or adjusted under 35 U.S.C. 154(b) by 0 days.

(21) Appl. No.: 13/721,215

(22) Filed: Dec. 20, 2012

Related U.S. Application Data

(63) Continuation-in-part of application No. 12/853,842, filed on Aug. 10, 2010.

(51) Int. Cl.
| | |
|---|---|
| *A61K 31/74* | (2006.01) |
| *A61L 15/44* | (2006.01) |
| *A61L 15/60* | (2006.01) |
| *A61K 33/26* | (2006.01) |
| *A61K 31/79* | (2006.01) |

(52) U.S. Cl.
CPC ............... *A61K 31/79* (2013.01); *A61K 33/26* (2013.01)
USPC .................................. 424/78.06; 424/78.07

(58) Field of Classification Search
CPC ... A61L 2300/202; A61L 15/44; A61L 15/60; A61L 2300/106; A61K 31/74
USPC ........................................... 424/78.06, 78.07
See application file for complete search history.

(56) References Cited

U.S. PATENT DOCUMENTS

| | | | |
|---|---|---|---|
| 5,942,218 | A | 8/1999 | Kirschner et al. |
| 6,187,347 | B1 | 2/2001 | Patterson et al. |
| 6,267,896 | B1 | 7/2001 | Patterson et al. |
| 6,521,265 | B1 | 2/2003 | Patterson |
| 6,638,143 | B2 | 10/2003 | Wang et al. |
| 8,110,208 | B1 | 2/2012 | Hen |
| 8,361,504 | B2 | 1/2013 | Hen et al. |
| 8,372,441 | B2 | 2/2013 | Thompson et al. |
| 2010/0226873 | A1 * | 9/2010 | Hen et al. ............... 424/78.06 |

FOREIGN PATENT DOCUMENTS

RU    2125453 C1 * 1/1999

OTHER PUBLICATIONS

Turton et al. Target Organ Pathology. London: Taylor & Francis Ltd., 2005. p. 18.*
International Specialty Products, "PVP-Iodine Povidone Iodine Antiseptic Agent", 2004, p. 9.
RW Lacey, J Appl Bacteriology, vol. 46, Issue 3, p. 443-449, Jun. 1979, "Antibacterial Activity of Povidone Iodine towards Non-sporing Bacteria".
Munoz et al., "*Saccharomyces cervisiae* fungemia: an emerging infectious disease", Clin Infect Dis 2005:40:1625-34.
Herbrecht et al., Clin Inf Dis 2005:40:1635-1637, "SC fungemia—an adverse effect of *S boulardi* Probiotic Administration".
Venugopalan et al., Emerging Infect Dis vol. 16 (11) Nov. 2010, "Regulatory oversight and safety of probiotic use".
K. Kuorwel et al., Packaging Tech & Sci, vol. 24, Issue 5, "Antimicrobial Activity of Natural Agents against *Saccharomyces cerevisiae*", 2014.
Medline Plus, http://www.merriam-webster.com/medlineplus/scab, 2014.
Hen, John, Oct. 29, 2008, Report of Pro QR Powder's Inherent Antimicrobial Activity.
Paulson, Daryl S., p. 90-91, 2003, Handbook of Topical Antimicrobials: Industiral Applications in Consumer.

* cited by examiner

*Primary Examiner* — Jeffrey S. Lundgren
*Assistant Examiner* — Chris Simmons
(74) *Attorney, Agent, or Firm* — Charles J. Prescott

(57) ABSTRACT

A composition and method useful in promoting hemostasis, absorbing ooze, and being antimicrobial with respect to an open wound. The composition broadly includes an antimicrobial agent, preferably povidone iodine, preferably a ferrate compound, and a cation ion exchange resin. This composition will destroy a biofilm which has formed over the open wound in providing a soluble iron compound, a cation chelation compound, and an active antimicrobial compound effective against planktonic microorganisms and biofilms. The antimicrobial agent is locked or sealed within the scab formed over the wound to maintain long-term positioning and anti-dilution of the antimicrobial over the wound.

4 Claims, 3 Drawing Sheets

FERRATE AND POVIDONE IODINE (PI) COMPOSITION

CROSS-REFERENCE TO RELATED APPLICATIONS

Not applicable

STATEMENT REGARDING FEDERALLY SPONSORED RESEARCH OR DEVELOPMENT

Not applicable

INCORPORATION-BY-REFERENCE OF MATERIAL SUBMITTED ON A COMPACT DISC

Not applicable

BACKGROUND OF THE INVENTION

1. Field of the Invention

This invention relates generally to hemostatic and antimicrobial barrier composition that achieves persistent antimicrobial properties by trapping the antimicrobial agent in a seal formed by the interaction of the hemostatic agent and blood and/or exudates, and particularly to a hemostatic composition comprising a ferrate compound and a cationic ion exchange resin with an antimicrobial agent, preferably povidone iodine which is hemostatic, antimicrobial and serves as an exudent.

2. Description of Related Art

Povidone iodine (PI) is well known as a broad spectrum, fast-acting antimicrobial compound. The USFDA Temporary Final monograph, incorporated in its entirety by reference, describes the efficacy of 5 to 10% PI solutions as an antimicrobial active.

Potassium ferrate (ferrate) is also a well-known disinfectant compound as a result of its very strong oxidation potential, disclosed in U.S. Pat. Nos. 6,187,347, 6,267,896 and 6,521,265 by Patterson et al. incorporated in their entirety.

Mixtures of ferrate and dry resin are also well known, disclosed in Patterson et al. in U.S. Pat. No. 6,187,347 and sold commercially as BIOSEAL (now WOUNDSEAL) powder. Mixtures of ferrate and dry acidic cationic exchange resin (1:7 ratio) are used as a safe and effective hemostasis powder. This compound is formed of a salt taken from the group consisting of H, Li, Na, K, Rb, Cs and Fr. However, to decrease or eliminate stringing sensation, the compound may be formed having a salt taken from the group consisting of Be, Mg, Ca, Sr, Ba, Ra, Ti, V, Cr, Mn, Fe, Co, Ni, Cu, Zn, Ga, Ge, Zr, Nb, Mo, Tc, Ru, Rh, Pd, Ag, Cd, In, Sn, Hf, Ta, W, Re, Os, Ir, Pt, Au, Hg, TI, Pb, Bi, Al, As, $NH_4$ and $N(C_4H_9)_4$. The preferred composition also includes a cation exchange material such as sulfonated ion exchange resin as an admixture which will hydrate in the presence of blood and other body fluids to produce $Fe^{+++}$ thereby promoting clotting of the blood and body fluid and to produce oxygen.

BIOSEAL (now WOUNDSEAL) trademarks of Biolife, L.L.C. of Florida is an amazingly effective antibacterial powder. It dries colonizing bacteria and extracts cations from the cell wall, replacing the cation with a proton and dropping the pH to about 2. It is well known that most bacteria are killed at that pH. Testing shows a slight kill for Candida, but essentially no kill for *Aspergillus*. Thus the BIOSEAL (now WOUNDSEAL) powder would have antibacterial efficacy, but not antimicrobial efficacy.

Other antimicrobial actives, such as chlorhexidine gluconate (CHG), are reported to have antibacterial and antimicrobial efficacy. CHG is also reported to be more effective than povidone iodine by the Centers for Disease Control (CDC). If an iodine product is to be competitive, it has to be better than CHG, cheaper, or have additional benefits that CHG does not have. For example, CHG loses efficacy when there is modest bioburden in and around the treated site; iodine does not. CDC guidelines for BIOPATCH, a 2% CHG-impregnated patch, require a dressing change if there is oozing.

A product that provides for hemostasis, absorbing ooze without compromising antimicrobial efficacy, and is also a powder would be particularly advantageous.

The foregoing examples of the related art and limitations related therewith are intended to be illustrative and not exclusive. Other limitations of the related art will become apparent to those skilled in the art upon a reading of the specification and a study of the drawings.

BRIEF SUMMARY OF THE INVENTION

This invention is directed to a composition useful in promoting hemostasis, absorbing ooze, and being antimicrobial with respect to an open wound, as well as providing a persistent antimicrobial activity after hemostasis has been achieved by trapping the added antimicrobial agent within the seal formed over the wound as a result of the interaction by blood and the hemostatic agent during hemostasis. The composition broadly includes a salt ferrate compound, a cation exchange resin and an added antimicrobial agent. The preferred composition includes povidone iodine as the preferred added antimicrobial, and potassium ferrate as the salt ferrate compound and cation exchange resin in the hydrogen or acid form. This composition will destroy a biofilm which has formed over the open wound. This composition also provides an antimicrobial action against planktonic microorganisms and biofilms.

This disclosure is broadly directed to a combination of an antimicrobial agent and a hemostatic product. When the combination is applied to a bleeding wound, the hemostatic product stops the bleeding, becomes incorporated into the scab and locks the antimicrobial agent to the wound. The product can be designed to lock the antimicrobial agent at the surface of the blood or to penetrate through the blood to the wound surface. This can be accomplished by either a chemical means of manipulating the combined products or by a mechanical means of designing a bandage with the antimicrobial agent beneath the hemostatic agent.

One major aspect of this disclosure is to prevent the antimicrobial agent from being easily removed from the wound. Powders are easily brushed or washed away, or eroded away with flowing blood. Sprays are easily wiped or washed away or eroded by flowing blood. Creams and ointments can be messy and washed away and can't be applied to an actively bleeding site.

This composition stops the flowing blood and combines with the blood to lock the antimicrobial agent at the wound. Because the flow of blood is stopped, the antimicrobial agent will not be diluted to the point of non-effectiveness or worse to such a low level that doesn't kill all of the microbes and creates resistant microbes, a most important aspect of this disclosure.

On non-actively bleeding wounds, this composition combines with the exudates to create a seal to prevent the desiccation of the wound, while absorbing excess exudates (preventing maceration), and locking an antimicrobial agent at the surface of the wound to assist with wound healing.

DETAILED DESCRIPTION OF THE INVENTION

This disclosure is broadly directed to a composition of hemostatic agent(s) to which an antimicrobial agent is added. The total composition stops bleeding/exudation and provides a persistent antimicrobial barrier. The hemostatic agent(s) stops bleeding from an open wound and absorbs exudates emanating from the wound. During hemostasis, a strong seal is formed between the hemostatic agent(s) and the blood that traps the added antimicrobial agent in the seal. After hemostasis, the formation of the seal sets the antimicrobial in close contact with wound and allows the antimicrobial to form a persistent antimicrobial barrier to provide faster healing of the wound.

Figure 5:
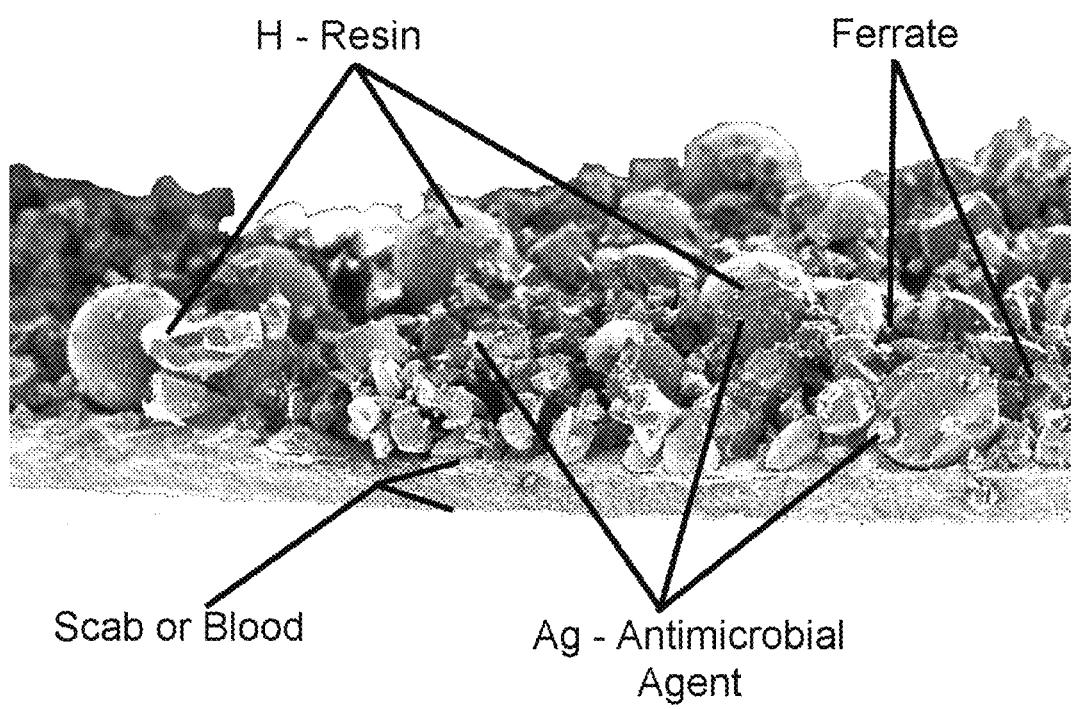
FIG. 5 is a scanning electron microscope (SEM) of a cross-section of ferrate, resin, and an antimicrobial agent (Ag) sealed within a scab of blood formed by the resin.

The preferred composition exemplified by the hemostatic agent includes a ferrate compound and a cation exchange resin, and povidone iodine as the added antimicrobial agent. However, the ferrate compound is optional in another embodiment. An SEM picture illustrating the trapping of an added silver antimicrobial agent to a hemostatic seal can be seen in FIG. 5. In the picture, the seal is formed between blood and ferrate/cation exchange resin (hemostatic mixture). The SEM picture shows the ferrate/resin/Ag Antimicrobial Agent mixture adhered to a thin layer of dried blood. The combination of the powder and the blood is the "Seal". The setting of the antimicrobial agent in the seal allows the antimicrobial agent to remain active undiluted, and to exhibit persistency.

The seal can be seen above and close to, but separate from, the simulated "wound bed". Without the hemostatic mixture, the dried blood may form a scab, which may protect the wound. The hemostatic mixture significantly increases the speed of the scab/seal formation, while adhering the materials of the powder to the surface of the scab.

As can be seen in the SEM picture (FIG. 5) of the seal formed from blood and ferrate/cation exchange resin, it can easily be demonstrated that, when any antimicrobial agent (for example, povidone iodine) is added to hemostatic ferrate/cation exchange resin composition, the agent would be trapped in the seal. This trapping of the added antimicrobial agent allows it to be active in providing a persistent antimicrobial barrier. The addition of povidone iodine at 10% to the hemostatic ferrate/cation exchange resin composition does not affect the hemostatic efficiency in Example 4.

The counter ion on the cation exchange resin can be manipulated to reside either on the surface of the bleeding wound or sink below the surface. When the hydrogen form of the cation exchange resin is used, the hemostatic composition tends to stay on the surface of the bleeding wound, and therefore, the added antimicrobial would also reside on this surface. As the hydrogen form is replaced by sodium or calcium, the cation exchange resin sinks to the bottom of the bleeding wound, as will the added antimicrobial agent.

Any antimicrobial agent or mixture of antimicrobial agents can be employed in the practice of this disclosure. A wide range of antimicrobials includes: Chlorhexidine, Triclosan, Iodophors, Benzoyl Peroxide and other anti-acne agents, Hypochlorite, Mupirocin, Retapamulin, Dapsone, Neomycin and Gentamicin, Polymyxin and Bacitracin. The antimicrobial agent can take the form of a solid, a liquid adsorbed or absorbed on the cation exchange resin. The antimicrobial agent can be pre-adsorbed on a zeolite or any polymeric substrate. When the antimicrobial agent is in the anionic form, it can be adsorbed in the cation exchange resin.

Various manner of further promoting the longevity of the seal can be used such as spraying a powder after it is applied on the bleeding wound with a closing spray such as a cyanoacrylate spray. The antimicrobial agent can be added to the hemostatic agent composition:
either premixed with the hemostatic agent(s) or
sprayed onto the wound surface after the hemostatic agent(s) has been applied to the bleeding wound
a powdered form of the antimicrobial can be applied to the wound surface after the hemostatic agent(s) is first applied to the bleeding wound.

Povidone Iodine (PI)

Figure 1:
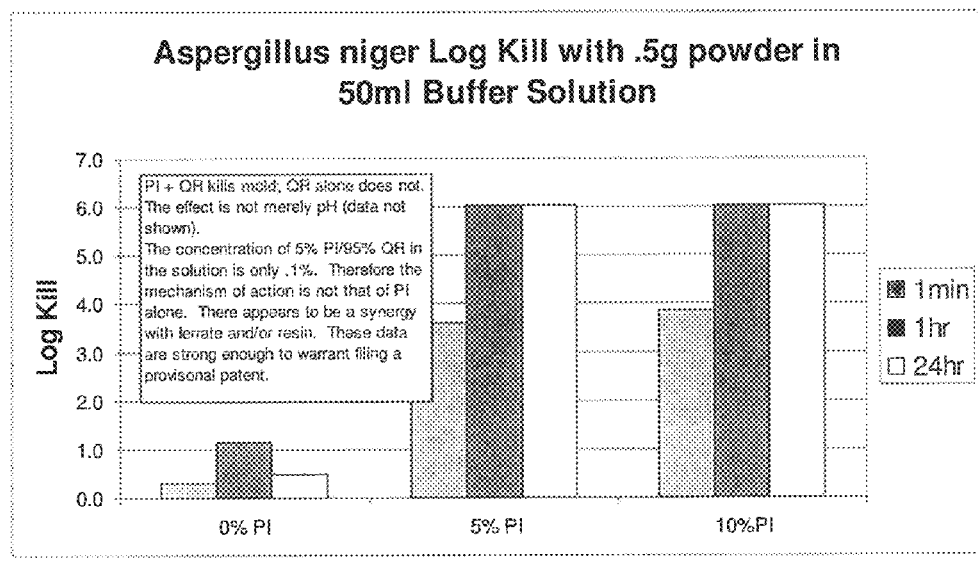
FIG. 1 shows *Aspergillus niger* log kill of 0.5 g powder in 50 ml. buffer solution.

A pamphlet, "PVP-IODINE Povidone Iodine Antiseptic Agent" (2004), by *International Specialty Products*, on page 9 therein, MODE OF ACTION, shows two charts. The top chart descriptor says: "In studies of PVP-Iodine solution equilibria, the content of uncomplexed iodine initially increases with dilution reaching a maximum at solution strength of 0.1% and decreases upon further dilution (FIG. 1). The other iodine species present in a PVP-Iodine solution exhibit normal behavior in that their concentration decreases on dilution."

Figure 2:
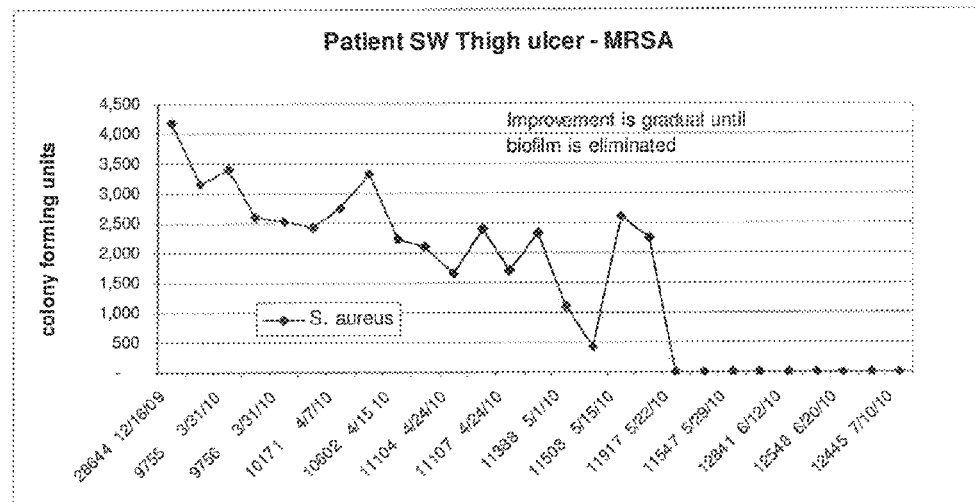
FIG. 2 shows the decay in MRSA colony growth over time.
Figure 3:
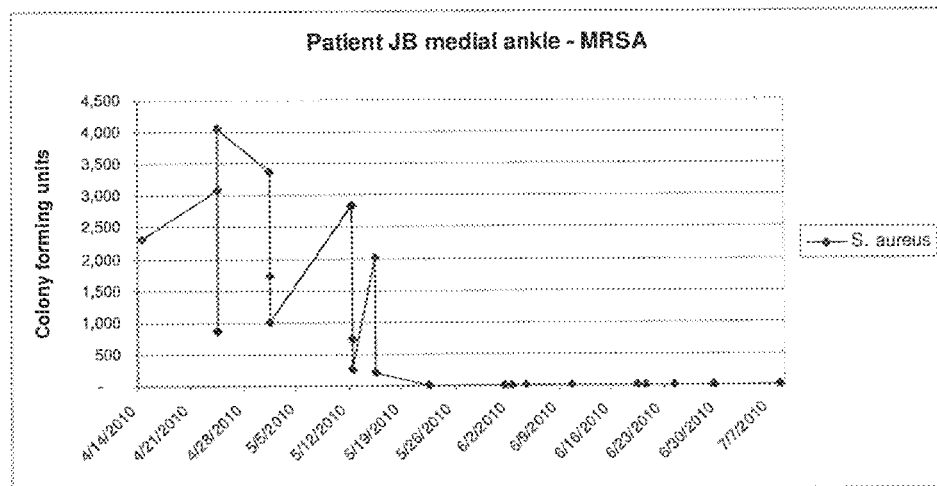
FIG. 3 shows the decay in MRSA colony growth over time for Example 1.
Figure 4:
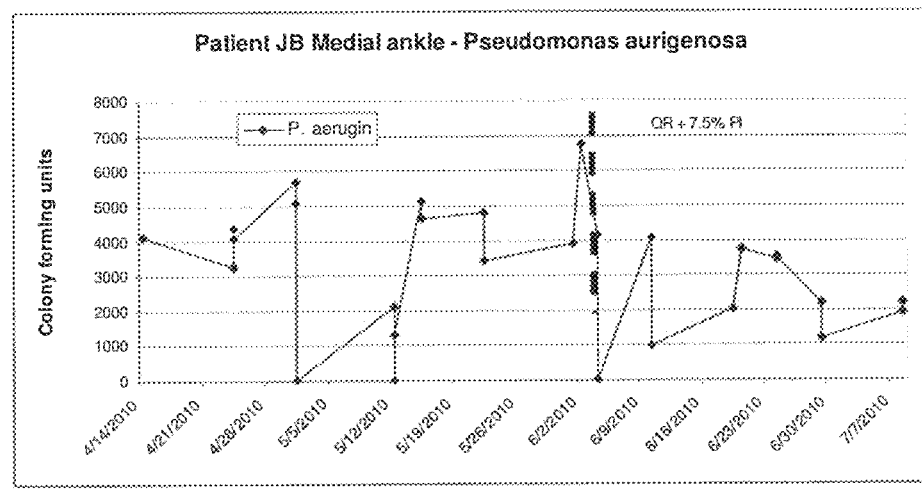
FIG. 4 shows the decay in *pseudomonas aurigenosa* colony growth over time for Example 1.

"Rackur explained this dilution phenomenon by the formation of polymeric aggregates which contain entrapped, uncomplexed iodine. Increasing the amount of solvent causes these aggregates to dissociate hence releasing the entrapped iodine and consequently increasing the antimicrobial efficacy of the solution". Examining FIG. 1 shows a broad plateau of substantially equivalent $I_2$ from 0.01% $I_2$ to 1% $I_2$, suggesting that PI is effective across a broad range of concentration but not as effective in the 5-10% range specified by FDA in the Antiseptic Monograph. In FIG. 2, the pamphlet shows that the $I_2$ species is the primary active ingredient and that the non-effective kill is at $I_2$ concentrations of <0.001%. At $I_2$ concentrations of between 0.005% and 1% PI, there is complete kill. However, concentrations of between 5-10% PI are ineffective, but a slow release of low dose $I_2$ can be effective if the released amount is between 0.005% and 1% PI.

Chemical Structure of PI

PVP-Iodine is a stable chemical complex of Polyvinylpyrrolidone and elemental iodine having the chemical formula:

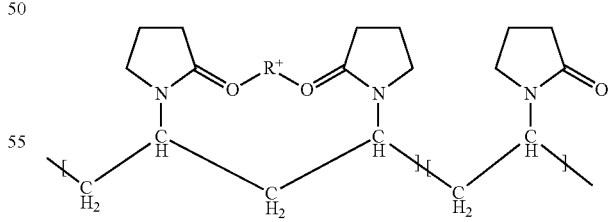

Surprisingly, admixtures of PI and ferrate and strong acid cation exchange resins do provide a multitude of benefits. In vitro testing with EDTA-treated bovine blood and BIOSEAL (WOUNDSEAL) powder with and without PI showed no difference in seal strength when the PI was 5-10% of the powder. The PI is stable in this very dry environment.

A mixture of soluble iron, a cation chelation means, and an active antimicrobial compound had a surprising effect on biofilms. Without wishing to be bound, ferrate decomposition creates soluble $Fe^{3+}$; the iron displaces the $Ca^{++}$ in the EPS, destabilizing the protective outer shroud. The cation exchange resin captures the $Ca^{++}$ and lowers pH. The biofilm is dispersed. The absorbed liquids dissolve a fraction of the povidone iodine. The low level of free iodine is lethal to the now-freed, planktonic bacteria. The iron disrupts the biofilm; the resin indirectly disperses the biofilm; the free iodine destroys released-bacteria.

Other sources of soluble iron can do what the ferrate does. Other chelators like EDTA, tripoly phosphate, sodium nitrilotriacetate (NTA), and stearic acid can sequester calcium. Other antiseptics like CHG, benzethonium chloride, benzalkonium chloride, >62% alcohol and PHMB can kill planktonic bacteria.

An experiment was run with diluted BIOSEAL (now WOUNDSEAL)/PI admixture and a buffered phosphate solution and then standard micro testing was conducted on *Aspergillus Niger*, a mold which is hard to kill.

Three powders were tested:
a) 100% BIOSEAL (now WOUNDSEAL)
b) 95% BIOSEAL (now WOUNDSEAL) 5% PI
c) 90% BIOSEAL (now WOUNDSEAL) 10% PI These quantities, 0.1, 0.5, 2.0 g, of powder were poured into 50 ml of buffer solution. The kill was determined over time. Table I shows that even significantly reduced mass of BIOSEAL (now WOUNDSEAL) had almost complete kill of the E-Coli. Table II shows that BIOSEAL (now WOUNDSEAL) alone has little effect on the mold. However, the addition of PI killed mold when using 0.5 g or 2.0 g., whereas 0.1 g of either mixture was insufficient to kill mold.

TABLE I

E-Coli Plate Count
Microbac Labs Results

| | 0.1 g | 0.5 g | 2.0 g | Control |
|---|---|---|---|---|
| 100% BIOSEAL (now WOUNDSEAL) 0% PI ||||
| 1 min | 2,000 | — | — | 1,500,000 |
| 1 hr | 220 | — | — | 1,500,000 |
| 24 hr | — | — | — | 340,000 |
| pH | 6.29 | 2.72 | 2.49 | |
| 95% BIOSEAL (now WOUNDSEAL) 5% PI ||||
| 1 min | 1 | — | — | 1,500,000 |
| 1 hr | — | — | — | 1,500,000 |
| 24 hr | — | — | — | 340,000 |
| pH | 6.33 | 2.8 | 2.35 | |
| 90% BIOSEAL (now WOUNDSEAL) 10% PI ||||
| 1 min | 1,500 | — | — | 1,500,000 |
| 1 hr | 220 | — | — | 1,500,000 |
| 24 hr | — | — | — | 340,000 |
| pH | 6.4 | 2.98 | 2.34 | |

0.1, 0.5, & 2.0 grams of powder into 50 ml of buffer solution.
The above-referenced pamphlet states that 5% PI is more effective than 10% PI on bacteria. The Table 1 results confirm this teaching.

TABLE II

Mold Plate Count
Microbac Labs Results

| | 0.1 g | 0.5 g | 2.0 g | Control |
|---|---|---|---|---|
| 100% BIOSEAL (now WOUNDSEAL) 0% PI ||||
| 1 min | 1,000,000 | 600,000 | 1,400,000 | 1,200,000 |
| 1 hr | 120,000 | 80,000 | 1,600,000 | 1,100,000 |

TABLE II-continued

Mold Plate Count
Microbac Labs Results

| | 0.1 g | 0.5 g | 2.0 g | Control |
|---|---|---|---|---|
| 24 hr | 800,000 | 350,000 | 600,000 | 1,100,000 |
| pH | 6.29 | 2.72 | 2.49 | |
| 95% BIOSEAL (now WOUNDSEAL) 5% PI ||||
| 1 min | 500,000 | 300 | — | 1,200,000 |
| 1 hr | 50,000 | — | — | 1,100,000 |
| 24 hr | 80,000 | — | — | 1,100,000 |
| pH | 6.33 | 2.80 | 2.35 | |
| 90% BIOSEAL (now WOUNDSEAL) 10% PI ||||
| 1 min | 87,000 | 170 | — | 1,200,000 |
| 1 hr | 15,000 | — | — | 1,100,000 |
| 24 hr | 25,000 | — | — | 1,100,000 |
| pH | 6.40 | 2.98 | 2.34 | |

0.1, 0.5, & 2.0 grams of powder into 50 ml of buffer solution.
10% PI is more effective than 5% PI on mold.

The actual concentration of PI in the buffer solution was very much lower than PI in current antimicrobial formulations. For example, The Temporary Final Monograph (TFM) states the PI is active @ from 5 to 10%. In this test, 0.5 g powder in 50 ml of buffer solution is 0.1% PI, a 98% reduction in active ingredient, yet it was still active on *Aspergillus*. There was little kill with 0.1 g @ 1 minute, but 3.5 log kill at 1 minute with 0.5 g powder and 2 g powder. With 0.1 g of 10% PI, the buffered pH was 6.4 and there was a 4.9 log kill of *Aspergillus*, indicating that the mechanism of action is not merely pH. (See FIG. 1)

The observation that the action is not primarily a pH response and that ultra low doses are effective in very short time periods demands explanation. What was found is that the novel combination of potassium ferrate, strong acid cationic ion exchange resin and povidone iodine provides, very fast time to hemostasis, antimicrobial activity, and a low pH environment which helps skin below the clot to be healthy and smooth.

Other cations can be used as the ferrate counter ion as disclosed in the previously referenced Patterson et al. patents. Preferred applications are for perforated skin: arteriotomy, vascular access, sutures, staples, traumatic injury, battlefield wounds etc. The powder form provides a scrubbing benefit, particularly useful in skin preparation before surgery. The skin's moisture activates the iodine; the powder exfoliates the skin. Dead skin is removed and remaining viable skin is sanitized.

In other experiments, the decomposition of BIOSEAL (now WOUNDSEAL) powder in water increased the iron concentration in the supernatant. Ferrate is soluble, $Fe_2O_3$ iron oxide is not at neutral pH. Iron chemistry and iodine chemistry in water is complex. Iron will react with iodine:

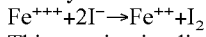

This reaction implies that soluble $Fe^{+++}$ from the decomposition of $Fe^{6+}$ can convert inactive iodide into active iodine. This is a possible mechanism for explaining the surprising efficacy of the ferrate/resin/PI mixture.

Biofilms

Biofilms are ubiquitous in nature and are the means by which bacteria insure their survival. A bacterium will bind to a substrate. Once anchored, mixed colonies of bacteria will build a colony of partially vertical structures designed to scavenge scarce nutrients and distribute them throughout the structure. The structure is mechanically protected by exopolysaccharide structures (EPS) which are stabilized by $Ca^{++}$ (and magnesium) cross-linking. Bacteria in biofilms signal to one another until they sense a quorum. When a quorum is sensed, the bacteria spew out toxins to induce the host to produce exudate (food for the biofilm).

The ferrate/resin/povidone iodine mixture is surprisingly effective at disrupting, dispersing and destroying biofilms in chronic wounds. Biofilms are organized colonies of mixed bacteria designed to prevent killing of the bacteria. In a greatly simplified explanation, biofilms are formed:

1. First reversibly and then permanently bonding sacrificial bacteria to the host
2. Vertical structures of living bacteria grow above the bonded dead bacteria.
3. The intermediate bacteria are kept alive, but are intentionally deprived (starved) of nutrients. By starving, they do not absorb lethal doses of antibiotics and thus can survive an antibiotic attack.
4. The vertical structure has fluid pathways to bring limited nutrients to the intermediate bacteria and to remove waste products.
5. The structure is capped by an exopolysaccharide shield (EPS) that is reinforced by calcium binding to the carboxylic acid moiety in the polysaccharides which protects the biofilm from attack by surface disinfectants and antiseptics.
6. Benign biofilm continues to grow until a quorum is sensed, at which time the pathogens spew forth toxic chemicals.
7. The host registers the toxins as foreign bodies and mounts an exudate-laden counter attack.
8. The EPS structure deflects the attack and captures proteins-in-exudate as "biofilm food". The net effect is that poisoning the host is a strategy to generate food for growth and survival.

Destruction of Biofilm

Without wishing to be bound, it is believed that the ferrate/resin/povidone iodine mixture disrupts, disperses and destroys the biofilm in multiple ways:

1. As the ferrate dissolves into $Fe^{3+}$, the iron displaces the $Ca^{++}$ in the EPS, changing the geometry of the EPS shield.
2. The resin adsorbs $Ca^{++}$ in exchange for H. The consequent lower pH increases the solubility of $Fe^{+++}$ and $Ca^{++}$.
3. The EPS structure is disabled and the "roof" of the biofilm is disrupted.
4. Some of the underlying bacteria escape the disintegrating structure and become planktonic.
5. Once planktonic, the bacteria are susceptible to iodine attack.
6. Compared to in vitro testing, this is a very slow iterative process.
7. By packing a wound with excess powder such that the proximal surface is damp and the distal surface is dry, there is a slow release of iodine.
8. The response of badly infected in vivo wounds is not rapid; a little is removed each treatment.

The sulfonated ion exchange resin in Patterson is not a cation chelating resin. As defined by Rohm and Haas, a major resin manufacturer:

1. An ion-exchange resin is an insoluble polymeric matrix containing labile ions capable of exchanging with ions in the surrounding medium. They can be grouped into 4 general categories: strong acid, weak acid, strong base and weak base. There is no complexation or chelation involved in the present invention, but only electrostatic interaction.
2. Chelating resins have special functional groups which contain 2 or more electron donor atoms that can form coordinate bonds to a single metal atom. Classes of chelating functional groups of industrial importance are phosphonic acids, amino-, carboxylic acids and sulfur compounds. Resins that have metal chelating capabilities include those containing aminophosphonic acid or imininodiacetic acid or thiol sites.

Therefore, the sulfonated ion exchange resin of Patterson is not a chelating resin.

Antimicrobials

There are many types of antimicrobial, antibacterial, bacterialstatic, etc. products on the market, all of which are referred to herein as "antimicrobial agents". These antimicrobial agents may be injected, taken intravenously, inhaled, or are topical, the focus of the present invention being topical in nature. There are many types of topical antimicrobial agents; creams, powder, ointments, sprays, or in combination with a bandage. These products when applied to a wound need to be covered to present the product from being removed from the wound.

Example 1

Not all pathogens react the same way. Patient JB presented with multi-drug resistant lateral and medial wounds on the right leg. JB had been hospitalized several times and discharged without complete healing. He presented with gross necrotic tissue and biofilm. The first time his wound was unwrapped, 4 fl. oz. of exudate was recovered. These wounds were the most severe wounds the clinic had seen. Three different doctors instructed JB to go to the hospital for amputation.

The patient refused and asked for treatment outside the hospital. With informed consent, he agreed to a series of sequential interventions to determine how to heal his wounds. BIOSEAL (now WOUNDSEAL) was packed into JB's ankle wounds and wrapped traditionally. There was excess exudate, so the frequency of changing the dressing was increased to 3 times per week.

BIOSEAL (now WOUNDSEAL) without PI was effective at serially reducing MRSA, but was ineffective on *Pseudomonas*. 7.5% PI was added and *Pseudomonas* levels were reduced, but not eliminated. The PI level was increased to 10% and the *Pseudomonas* was eliminated.

Explanation of Example 1

Experts describe the resilience of in-vivo biofilms versus in-vitro antimicrobial testing as almost three orders of magnitude greater in a biofilm than as planktonic bacteria. Thus, an in-vitro test demonstrates efficacy that does not translate to efficacy in practice. MRSA is easier to kill than *Pseudomonas* in mature biofilms in-vivo. The iodine had to be increased all the way to 10% before *Pseudomonas* was killed.

The powder is packed into the wound such that the proximal side is damp and the distal side is dry. Dry PI does not release $I_2$ to the wound site. Thus, as the powder gets increasingly damp, there is a slow release of $I_2$. More iodine is not more lethal. In fact, iodine is most lethal at very low levels. What iodine leaching from damp powder does is extend the time that lethal low levels of iodine are exposed to the biofilm.

The ferrate dissolves in exudate and releases a free $Fe^{3+}$. The iron displaces the calcium reinforcing the EPS, disrupting the physical geometry of the EPS shield. The released calcium ion is adsorbed into the resin and a proton is released, dropping the pH. At pH 2, the calcium remaining in the biofilm is partially released. The net effect is to disrupt the biofilm. To visualize the effect, the biofilm is not destroyed, but its "roof" is removed, exposing the bacterial inhabitants to attack by iodine.

"De-roofing" the biofilm continuously exposes more and more intermediate bacteria to attack by iodine. Over time, one roof at a time, the biofilm is disrupted, dispersed and destroyed. The swab data show a linear decline as the biofilm is dispersed until a precipitous decline occurs when the remaining biofilm is destroyed.

Example 2

The potassium ferrate was replaced with magnetite, $Fe_2O_4$. Magnetite is a more soluble form of iron oxide, but the iron is $Fe^{4+}$. Magnetite, resin and 10% PI were mixed together and tested in vivo on drug-resistant wounds. MRSA was killed, but *Pseudomonas* was not.

Explanation of Example 2

$Fe^{3+}$ regenerates iodine from iodide and converts into $Fe^{2+}$ as shown above. $Fe^{4+}$ does not have this reaction. Thus, the ferrate is a source of soluble $Fe^{3+}$, increasing the net duration of free iodine availability. With extended free iodine availability, *pseudomonas* is destroyed. What is surprising is that an indirect source of soluble $Fe^{3+}$, a divalent cation sequestering agent (resin, poly phosphate, fatty acid etc) and a source of free iodine ($I_2$) and iodide ($I^-$) can disrupt, disperse and destroy multi-drug resistant biofilms in vivo.

Example 3

Patient WU has a venous ulcer that required debriding of biofilm three times per week, but the wound still did not heal. She was treated with the ferrate/resin/10% API powder. Biopsies and detailed analysis of the wound bed demonstrated a statistically significant reduction in biofilm with the powder versus sharp debridement.

A sample of the biofilm was extracted from WU and transferred to a 96 count plate and new biofilms grown from WU genetic material. The powder was applied to the in vitro biofilm and complete kill of the biofilm was achieved at various concentrations.

Explanation of Example 3

WU is a patient at a medical college wound clinic. With informed consent, WU was treated in vivo, but her biofilm was captured and grown into biofilm in a controlled reproducible fashion. The in vitro work is a work in progress as of this filing. The work is intended to elucidate the exact mechanism of action postulated elsewhere in this specification. Even at this early date, the work confirms the clinical in vivo findings.

Example 4

A mixture of various iron sources, chelation compounds, and active antimicrobials was tested using the recovered biofilm from WU according to the matrix in Table III.

TABLE III

| | Iron Source | Chelator | Active Antiseptic | Hemostasis Rating (1-10) | Biofilm Eradication (1-10) |
|---|---|---|---|---|---|
| 1 | Fe2O3 | tripoly phosphate | 10% PI | 2 | 7 |
| 2 | Fe2O3 | stearic acid | 10% PI | 1 | 4 |
| 3 | Fe2O3 | EDTA | 10% PI | 4 | 8 |
| 4 | Fe2O3 | cation exchange resin | 10% PI | 6 | 9 |
| 5 | Fe2O3 | tripoly phosphate | benzethonium chloride | 1 | 7 |
| 6 | Fe2O3 | stearic acid | benzethonium chloride | 2 | 4 |
| 7 | Fe2O3 | EDTA | benzethonium chloride | 5 | 6 |
| 8 | Fe2O3 | cation exchange resin | benzethonium chloride | 8 | 9 |
| 9 | ferrate | tripoly phosphate | 10% PI | 6 | 9 |
| 10 | ferrate | stearic acid | 10% PI | 5 | 4 |
| 11 | ferrate | EDTA | 10% PI | 6 | 8 |
| *12 | ferrate | cation exchange resin | 10% PI | 10 | 10 |
| 13 | ferrate | NTA | 10% PI | 6 | 8 |
| 14 | ferrate | tripoly phosphate | 70% ethanol | 1 | 5 |
| 15 | ferrate | stearic acid | 70% ethanol | 1 | 3 |
| 16 | ferrate | EDTA | 70% ethanol | 1 | 6 |
| 17 | ferrate | cation exchange resin | 70% ethanol | 3 | 7 |

Each mixture was tested in a standard hemostasis strength device described in detail in FDA 510k filing, K080210, incorporated herein in its entirety, and in the standardized 96 unit biofilm eradication test device also described in the 510k filing. The results were indexed* to #12, the ferrate/resin/10% PI powder.

Explanation of Example 4

The results are presented indexed* to the ferrate/resin/10% PI powder tested in vivo. The protocol was not designed to optimize any of the alternate variations, but rather to show that the mixture of a soluble iron source/chelation compound/active antimicrobial compound is a general mixture not a specific mixture. The hemostasis value for alcohol and ferrate, for example, is low because the water in the alcohol decomposed the ferrate. The acidic mixtures perform better in biofilm eradication because the low pH helps dissolve the iron source.

Example 5

Patient EM, a lymphedema patient with 3 DVT's in his leg, presented with a 6.8 cm×4.5 cm×0.2 cm venous ulcer the shape of the African Continent on his shin. After only 8 days treatment with the powder, the wound volume was reduced 11.1% and his exudate production was reduced significantly.

TABLE IV

| Source | Date | ccrBIII | ccrBIV | MRCoNs | Amino-glycoside | Erythro-mycin | Tetra-cycline | E faecalis | Pseudo-monas | Serratian | Strepto-coccus pyogene |
|---|---|---|---|---|---|---|---|---|---|---|---|
| | Jan. 9, 2010 | 37 | 39 | ND | ND | ND | 5808 | ND | ND | 2426 | 3714 |
| | Apr. 28, 2010 | 1549 | 970 | 772 | 1762 | 3358 | 5364 | 604 | ND | 3538 | ND |
| Pre-microdine | May 5, 2010 | 77 | 78 | ND | ND | ND | 4364 | ND | ND | 3047 | ND |
| Post microdine | May 5, 2010 | 2330 | 2000 | 2269 | 1947 | 4994 4442 | 3996 | ND | ND | 3499 | ND |
| Post microcyn | May 5, 2010 | 1998 | 2149 | 1917 | 1889 | | 4224 | ND | ND | 2149 | ND |
| | Jul. 17, 2010 | 48 | 127 | ND | ND | ND | 224 | ND | 4982 | 2770 | ND |
| Pre peroxide | Jul. 29, 2010 | 62 | 73 | ND | ND | ND | ND | ND | 4860 | 1586 | ND |
| Post peroxide | Jul. 29, 2010 | 86 | 139 | 243 | ND | ND | ND | ND | 4130 | ND | ND |

Infectious Disease Doc Started Cipro

Explanation of Example 5

EM has three deep vein thrombosis clots in his leg and compression therapy is not an option. The wound was producing gross exudate. EM was hospitalized and treated with IV antibiotic treatment and Cipro, antibiotics designed to kill *P. Auriginosa*. The effect was opposite to the intent and resistant *P. auriginosa* infected the wound after hospitalization.

The powder gradually lowered the *Pseudomonas* during the 8 days of therapy and healing began. EM is a work in progress.

Example 6

A 1,500 bed hospital modified its central line insertion protocol to apply the ferrate/resin/PI mixture upon insertion. After 6 months, the infection rate was 48% lower than an appropriate control period.

Explanation of Example 6

Central line insertions are notorious for relatively high infection rates versus PICC lines. There are two primary sources of infection, internal and external. In general, the internal infections are caused by ineffective cleaning of the hub through which access to the bloodstream is achieved. Biofilms form on the inside of the lumen and grow (migrate) down the inside of the line until the tip is reached. The biofilm colony extends past the tip of the line until it breaks off and infects the blood of the host.

External infections occur because the annular space between the line and the skin is breached and colonizing bacteria can penetrate the breach. Once in that annular space, they grow down the outside of the line to the end where they also break off and contaminate the bloodstream.

The mixture forms a nothing-in/nothing-out seal around the line and the skin. This mechanically prevents biofilm migration. In previous embodiments, without the active antimicrobial agent, the seal reduced catheter related blood stream infections (CRBSI) 40% of the time in PICC line insertions. When the active antimicrobial was added, the rate improved to 48% and in an inherently more contaminated environment (central lines versus PICC lines).

Example 7

A major hospital refused to use the ferrate/resin powder prophylactically on sutures and staples after operating room surgery. After the active antimicrobial agent was added, this hospital allowed the mixture as a prophylactic treatment to prevent leaking and oozing and prevent post surgery infection. Post surgical infections were reduced by 63%.

Explanation of Example 7

Hospitals are managed with interactive checks and balances to minimize systemic problems. Infectious disease gate-keepers would not allow use of the powder without an active antimicrobial ingredient in the OR. When the PI was added, the gate-keeper allowed the mixture in. Oozing sutures, staples and incisions no longer produced exudate and biofilms did not grow around the breaks in intact skin.

While a number of exemplary aspects and embodiments have been discussed above, those of skill in the art will recognize certain modifications, permeations and additions and subcombinations thereof. It is therefore intended that the following appended claims and claims hereinafter introduced are interpreted to include all such modifications, permeations, additions and subcombinations that are within their true spirit and scope.

The invention claimed is:

1. A composition for promoting hemostasis and protectively holding an antimicrobial agent over an open wound comprising:
    an anhydrous mixture of a cation ion exchange resin and the antimicrobial agent;
    wherein said antimicrobial agent is protectively locked or sealed within a portion of said mixture within a scab formed when said composition is applied over the wound wherein the antimicrobial agent is povidone iodine.

2. A composition for diminishing a biofllm which has formed over an open wound comprising:
    an anhydrous mixture of a cation exchange resin in the hydrogen form and an antimicrobial agent;
    wherein said antimicrobial agent is locked or sealed within a scab formed by said resin over the wound when said composition is placed atop the biofilm wherein the antimicrobial agent is povidone iodine.

3. A hemostatic composition for locking or sealing an antimicrobial agent within a scab formed over an open wound comprising:
    an anhydrous mixture of an antimicrobial agent, a cation exchange resin in the hydrogen form, and a ferrate salt compound;

said antimicrobial agent being locked or sealed within the scab to maintain persistent antimicrobial action wherein the antimicrobial agent is povidone iodine.

4. A composition for diminishing a biofilm which has formed over an open wound comprising:

an anhydrous mixture of an antimicrobial agent and a cation exchange resin in the hydrogen form;

said composition forming a scab over the wound when said composition is placed atop the wound, wherein the antimicrobial agent is locked or sealed within the scab, and wherein the antimicrobial agent is povidone iodine wherein the antimicrobial agent is povidone iodine.

* * * * *